US 6,541,271 B1
Apr. 1, 2003

(54) INFRARED SPECTROSCOPIC IMAGING OF LIBRARIES

(75) Inventors: Eric W. McFarland, San Jose; William Archibald, Hillsborough, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 08/946,135

(22) Filed: Oct. 7, 1997

Related U.S. Application Data

(63) Continuation-in-part of application No. 08/898,715, filed on Jul. 22, 1997, now Pat. No. 6,030,917.
(60) Provisional application No. 60/050,949, filed on Jun. 13, 1997, provisional application No. 60/048,987, filed on Jun. 9, 1997, provisional application No. 60/035,366, filed on Jan. 10, 1997, provisional application No. 60/035,202, filed on Jan. 10, 1997, provisional application No. 60/029,255, filed on Oct. 25, 1996, provisional application No. 60/028,106, filed on Oct. 9, 1996, and provisional application No. 60/028,105, filed on Oct. 9, 1996.

(51) Int. Cl.[7] .................. G01N 21/62; G01N 21/35; G01N 25/18
(52) U.S. Cl. .................. 436/171; 436/37; 436/147; 436/159; 436/164; 422/62; 422/93; 422/104; 422/196; 422/197
(58) Field of Search ............ 430/37, 147, 159, 430/164, 171, 172; 422/62, 93, 104, 196, 197

(56) References Cited

U.S. PATENT DOCUMENTS

| | | | |
|---|---|---|---|
| 3,431,077 A | | 3/1969 | Danforth |
| 3,933,044 A | * | 1/1976 | Loper et al. .............. 73/355 R |
| 4,099,923 A | | 7/1978 | Milberger |
| 4,928,254 A | * | 5/1990 | Knudsen et al. ........... 364/556 |
| 5,200,023 A | | 4/1993 | Gifford et al. |
| 5,344,236 A | | 9/1994 | Fishman |
| 5,534,698 A | | 7/1996 | Ohshima et al. |
| 5,776,359 A | * | 7/1998 | Schultz et al. ............. 423/263 |
| 6,063,633 A | * | 5/2000 | Willson, III ................. 436/37 |

FOREIGN PATENT DOCUMENTS

| | | | |
|---|---|---|---|
| EP | 0 535 881 A1 | | 4/1993 |
| GB | 2 194 847 A | | 3/1988 |
| WO | WO 97/32208 | | 9/1997 |
| WO | 97/43308 | * | 9/1997 |
| WO | 99/21957 | * | 5/1999 |
| WO | 99/34206 | * | 7/1999 |

OTHER PUBLICATIONS

J. Gasiot et al. *Nucl. Instrum. Methods* 1980, 175, 96–97.*
R. G. Johnson et al. *Anal. Calorim.* 1984, 5, 133–141.*
E. N. Lewis, et al. *Anal. Chem.* 1995, 67, 3377–3381.*
J. V. Jensen et al. in "Proc. Int. Congr. Catal. 6th" vol. 2, G. C. Bond et al, ed., 1977, Chemical Society, 796–805.*

(List continued on next page.)

*Primary Examiner*—Arlen Soderquist
(74) *Attorney, Agent, or Firm*—Dobrusin & Thennisch PC

(57) ABSTRACT

Methods and apparatus for screening diverse arrays of materials using infrared imaging techniques are provided. Typically, each of the individual materials on the array will be screened or interrogated for the same material characteristic. Once screened, the individual materials may be ranked or otherwise compared relative to each other with respect to the material characteristic under investigation. According to one aspect, infrared imaging techniques are used to identify the active sites within an array of compounds by monitoring the temperature change resulting from a reaction. This same technique can also be used to quantify the stability of each new material within an array of compounds. According to another aspect, identification and characterization of condensed phase products is achieved, wherein library elements are activated by a heat source serially, or in parallel. According to another aspect, a Fourier transform infrared spectrometer is used to rapidly characterize a large number of chemical reactions contained within a combinatorial library.

39 Claims, 6 Drawing Sheets

(1 of 6 Drawing Sheet(s) Filed in Color)

OTHER PUBLICATIONS

G. A. D'Netto et al. Int. Chem. Eng. Symp. Ser. 1984, 87, 247–254.*
J. Doppelbauer et al. Appl. Phys. B 1983, 33, 141–147.*
A Baiker et al. Can. J. Chem. Eng. 1985, 63, 138–145.*
S. Sharma et al. J. Catal. 1988, 110, 103–116.*
S. Lundgren et al. Rev. Sci. Instrum. 1994, 65, 2696–2703.*
X.-D Xiang et al. Science 1995, 268, 1738–1740.*
C. L. Hill et al. J. Mol Catal. A: Chem. 1996, 114, 103–111.*
S. Vignes et al, Compt. Rend. Congr. Ind. Gaz. 1961, 78, 405–411.*
K. Katayama et al, Bull. JSME 1969, 12, 1439–1447.*
U. Hoffmann et al, ACS Symp. Ser. 1978, 65, 189–200.*
E. Takegoshi et al, Int. J. Thermphys. 1984, 5, 219–228.*
J. L. Trostel Jr. et al, Proc. Int. Symp. Adv. Refract. Metall. Ind. 1988, 1, 41–52.*
S. M. J. Akhtar et al, NIST Spec. Publ. 1988, 752, 345–351.*
A. M. Hallen et al, Mod. Dev. Powder Metall. 1988, 21, 755–763.*
K. Inoue et al, Trans. JWRI 1989, 18, 73–77.*
R. C. Enck et al, Ceram Trans. 1990, 5, 214–221.*
D. L. Balageas et al, High Temp.—High Pressures 1991, 23, 517–528.*
A. Sasaki et al, Akita Kogyo Koto Gakko Kenkyu Kiyo 1992, 27, 11–18.*
T. Baba et al. Thermochim. Acta 1993, 218, 329–339.*
L. Vozar et al, High Temp.—High Pressures 1993, 25, 593–597.*
L. Kehoe et al, IEEE Trans. Compon., Packag., Manuf. Technol. part A, 1995, 18, 773–780.*
H. Wang et al, Ceram. Trans. 1996, 74, 609–618.*
H. Wang et al, Therm. Conduct. 1996, 23, 119–126.*
R. Brandt et al, High Temp.—High Pressures 1976, 8, 469–478.
K. Inoue Trans. JWRI 1991, 20, 35–40.
T. Mitsuhashi et al, Proceedings of the Fourth International Symposium on Advanced Nuclear Energy Research 1992, JAERI–M–92–207, 302–307.
L. I. Kiss et al, Dev. Appl. Ceram. New. Met. Alloys, Proc. Int. Symp. 1993, 143–154.
H. R. B. Orlande et al, Heat Transfer 1994, Proc. Int. Heat Transfer Conf., 10$^{th}$ 1994, 6, 403–408.
L. I. Kiss et al, Recent Metall. Adv. Light Met. Ind., Proc. Int. Symp. 1995, 415–421.
M. R. Kulkarni et al, HTD 1996, 327, 19–23.
Hoffmann et al. Chem. Abstr. 88, 111103x, Apr. 1978.*
T. Y. R. Lee et al, J. Heat Transfer, 100, 720–724, Nov. 1978.*
M. A. Bucknam et al. Trans. J. Br. Ceram. Soc. 82, 18–23, Jan. 1983.*
H. L. Lee et al, J. Am. Ceram. Soc. 68, C12–C13, Jan. 1985.*
S. M. J. Akhtar et al, Chem. Abstr. 110, 182454w, May 1989.*
A. Bernasconi et al, Rev. Sci. Instrum. 61, 2420–2426, Sep. 1990.*
G. S. Sheffield et al, Ceramic Bulletin, 70, 102–106, Jan. 1991.*
Ts Velinov et al, Meas. Sci. Technol. 1993, 4, 1266–1268.*
M. Reichling et al, J. Appl. Phyus. 75, 1914–1921, Feb. 1994.*
D. M. Todorovic et al, J. Appl. Phys. 76, 4012–4021, Oct. 1994.*
T. Kemp et al, Rev. Sci. Instrum. 66, 176–181, Jan. 1995.*
L. Fabbri et al. Rev. Sci. Instrum. 66, 3593–3600, Jun. 1995.*
J. E. Graebner Rev. Sci. Instrum. 66, 3903–3906, Jul. 1995.*
J. C. Lambropoulos et al, Polym. Preprints 37, 66–67, Aug. 1996.*
H. Wang et al, Chem. Abstr. 126, 66126x, Feb. 1997.*
N. V. Kul'kova et al. Khim. Prom. 44, 656–658, Sep. 1968.*
L. M. Gratton et al. Appl. Spectrosc. 32, 310–316, Jul. 1978.*
P. C. M. van Woerkom et al. Appl. Optics, 19, 2546–2550, Aug. 1980.*
D.R. Kember et al. J. Cem. Soc., Faraday Tans 2, 1981, 77, 1321–1329.*
M. M. McClory et al. J. Chem. Phys. 90, 628–633, Feb. 1986.*
G. Georgiades et al. Angew. Chem. Int. Ed. Engl. 26, 1042–1043, Oct. 1987.*
M. R. Prairie et al. J. Catal. 1991, 129, 130–144.*
B. S. Clausen et al. J. Catal. 1991, 132, 524–535.*
A. M. Vassallo et al. Appl. Spectrosc. 46, 73–78, Jan. 1992.*
D. Mazzarese et al. J. Electron. Mater. 21, 329–333, Mar. 1992.*
B. Wangmaneerat et al. Appl. Spectrosc. 46, 1447–1453, Oct. 1992.*
P. W. Morrison, Jr. et al. J. Vac. Sci. Technol., A 11, 490–502, Mar. 1993.*
J. A. Anderson J. Catal. 1993, 142, 153–165.*
K. S. Finnie et al. Chem. Aust. 60, 180–182, Apr. 1993.*
J. R. Markham et al. Appl. Spectrosc. 48, 265–270, Feb. 1994.*
R. Stangl et al. Proc.–SPIE 2255, 685–696, Apr. 1994.*
M. Takeuchi et al. Shigen to Kankyo 4, 429–434, Jun. 1995.*
H. Uetsuka et al. Surface Science 363, 73–78, Aug. 1996.*
Maldague, X. and S. Marinetti "Pulse Phase Infrared Thermography," J. Appl. Phys, 79[5]: 2694–2698, Mar. 1, 1996.
Philip W. Morrison, Jr., et al., "In Situ Infrared Measurements During Hot Filament CVD of Diamond in a Rotating Substrate Reactor," *Diamond and Related Materials,* vol. 5 (1996) pp. 242–246.
H. Hardisty, et al.; "Thermal Imaging in Electronics and Rotating Machinery," *British Journal of NDT,* vol. 36, No. 2, pp. 73–78.
Patent Abstracts of Japan, 07–226884, Naoki, Abstract Only.
Charles E. Berkoff, et al., "A Multiple Cell Apparatus for of Catalysed Chemical Reactions the Rapid Evaluation", *Chemistry and Industry,* vol. 17 (Jan. 1981), pp. 6869.
F.C. Moates, et al., "Infrared Thermographic Screening of Combinatorial Libraries of Heterogenous Catalysts", *Ind. Eng. Chem. Res.* (1996), vol. 35, pp. 4801–4803.
Bruce Posner, et al., "Catalytic Antibodies: Perusing Combinatorial Libraries", *TIBS,* vol. 19, (Apr. 1994), pp. 145–150.
J.T. Richardson, et al., "Characterization and Deactivation of NiO–THO$_2$", *Applied Catalysis,* vol. 48 (1989), pp. 159–176.
Hanak, J.J., "The 'Multiple–Sample Concept' in Materials Research: Synthesis, Compositional Analysis and Testing of Entire Multicomponent Systems," *Journal of Materials Sciences,* pp. 964–971 (1970).
Hanak, J.J., "Compositional Determination of rf Co–Sputtered Multicomponent Systems," *The Journal of Vacuum Science and Technology,* vol. 8, (1971). pp. 172–175.

* cited by examiner

INFRARED SPECTROSCOPIC IMAGING OF LIBRARIES

CROSS REFERENCE TO RELATED APPLICATIONS

This application is a continuation-in-part of commonly assigned U.S. patent application Ser. No. 08/898,715, filed Jun. 22, 1997, now U.S. Pat. No. 6,030,917 and claims benefit of commonly assigned, co-pending U.S. Provisional Applications Ser. No. 60/050,949, filed Jun. 13, 1997; No. 60/028,106, filed Oct. 9, 1996; No. 60/029,255, filed Oct. 25, 1996; No. 60/035,366, filed Jan. 10, 1997; No. 60/048, 987, filed Jun. 9, 1997; No. 60/028,105, filed Oct. 9, 1996; and No. 60/035,202, filed Jan. 10, 1997; the complete disclosures of which are incorporated herein by reference for all purposes.

This application is also related to commonly assigned, co-pending U.S. patent applications Ser. No. 08/327,513, filed Oct. 18, 1994, Ser. No. 08/438,043, filed May 8, 1995, and Ser. No. 08/841,423, filed Apr. 22, 1997; commonly assigned U.S. Provisional Application Ser. No. 60/016,102, filed Jul. 23, 1996; and PCT Application No. WO 95/13278, filed Oct. 18, 1995; the complete disclosures of which are incorporated herein by reference for all purposes.

FIELD OF THE INVENTION

The present invention generally relates to methods and apparatus for rapidly screening an array of diverse materials which have been created at known locations on a single substrate surface, and in particular to the combinatorial synthesis and characterization of libraries of diverse materials using IR imaging and spectroscopy techniques.

BACKGROUND OF THE INVENTION

The discovery of new materials with novel chemical and physical properties often leads to the development of new and useful technologies. Currently, there is a tremendous amount of activity in the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and reaction pathways for the synthesis of such solid state compounds.

The preparation of new materials with novel chemical and physical properties is at best happenstance with our current level of understanding. Consequently, the discovery of new materials depends largely on the ability to synthesize and analyze new compounds. Given approximately 100 elements in the periodic table that can be used to make compositions consisting of two or more elements, an incredibly large number of possible new compounds remains largely unexplored. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those collections for molecules having a desired property. An example of such a process is the humoral immune system which in a matter of weeks sorts through some $10^{12}$ antibody molecules to find one which specifically binds a foreign pathogen (Nisonoff et al., *The Antibody Molecule* (Academic Press, New York, 1975)). This notion of generating and screening large libraries of molecules has recently been applied to the drug discovery process.

Applying this logic, methods have been developed for the synthesis and screening of large libraries (up to $10^{14}$ molecules) of peptides, oligonucleotides and other small molecules. Geysen et al., for example, have developed a method wherein peptide syntheses are carried out in parallel on several rods or pins (*J. Immun. Meth.* 102:259–274 (1987), incorporated herein by reference for all purposes). Generally, the Geysen et al. method involves functionalizing the termini of polymeric rods and sequentially immersing the termini in solutions of individual amino acids. In addition to the Geysen et al. method, techniques have recently been introduced for synthesizing large arrays of different peptides and other polymers on solid surfaces. Pirrung et al. have developed a technique for generating arrays of peptides and other molecules using, for example, light-directed, spatially-addressable synthesis techniques (U.S. Pat. No. 5,143,854 and PCT Publication No. WO 90/15070, incorporated herein by reference for all purposes). In addition, Fodor et al. have developed a method of gathering fluorescence intensity data, various photosensitive protecting groups, masking techniques, and automated techniques for performing light-directed, spatially-addressable synthesis techniques (Fodor et al., PCT Publication No. WO 92/10092, the teachings of which are incorporated herein by reference for all purposes).

Using these various methods, arrays containing thousands or millions of different elements can be formed (U.S. patent application Ser. No. 08/805,727, filed Dec. 6, 1991, the complete disclosure of which is incorporated herein by reference for all purposes). As a result of their relationship to semiconductor fabrication techniques, these methods have come to be referred to as "Very Large Scale Immobilized Polymer Synthesis," or "VLSIPS™" technology. Such techniques have met with substantial success in screening various ligands such as peptides and oligonucleotides to determine their relative binding affinity to a receptor such as an antibody.

The solid phase synthesis techniques currently being used to prepare such libraries involve the sequential coupling of building blocks to form the compounds of interest. For example, in the Pirrung et al. method polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequence are synthesized. These solid phase synthesis techniques cannot readily be used to prepare many inorganic and organic compounds.

In PCT WO 96/11878, the complete disclosure of which is incorporated herein by reference, methods and apparatus are disclosed for preparing a substrate with an array of diverse materials deposited in predefined regions. Some of the methods of deposition disclosed in PCT WO 96/11878 include sputtering, ablation, evaporation, and liquid dispensing systems. Using the disclosed methodology, many classes of materials can be generated combinatorially including inorganics, intermetallics, metal alloys, and ceramics.

In general, combinatorial chemistry refers to the approach of creating vast numbers of compounds by reacting a set of starting chemicals in all possible combinations. Since its introduction into the pharmaceutical industry in the late 80's, it has dramatically sped up the drug discovery process and is now becoming a standard practice in the industry (*Chem. Eng. News* Feb. 12, 1996). More recently, combinatorial techniques have been successfully applied to the synthesis of inorganic materials (G. Briceno et al., *SCIENCE* 270, 273–275, 1995 and X. D. Xiang et al., *SCIENCE* 268, 1738–1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors. Discovery of heterogeneous catalysts will no doubt be accelerated by the introduction of such combinatorial approaches.

A major difficulty with these processes is the lack of fast and reliable testing methods for rapid screening and optimization of the materials. Recently, a parallel screening method based on reaction heat formation has been reported (F. C. Moates et al., *Ind. Eng. Chem. Res.* 35, 4801–4803, 1996). For oxidation of hydrogen over a metallic surface, it is possible to obtain IR radiation images of an array of catalysts. The hot spots in the image correspond to active catalysts and can be resolved by an infrared camera.

Screening large arrays of materials in combinatorial libraries creates a number of challenges for existing analytical techniques. For example, traditionally, a heterogeneous catalyst is characterized by the use of a micro-reactor that contains a few grams of porous-supported catalysts. Unfortunately, the traditional method cannot be used to screen a catalyst library generated with combinatorial methods. First, a heterogeneous catalyst library synthesized by a combinatorial chemistry method may contain from a few hundred to many thousands of catalysts. It is impractical to synthesize a few grams of each catalyst in a combinatorial format. Second, the response time of micro-reactors is typically on the order of a few minutes. The time it takes to reach equilibrium conditions is even longer. It is difficult to achieve high-throughput screening with such long response times.

Another challenge with screening catalyst arrays is the low level of components that may be present in the reactions. The consequence of low level catalytic material is a low conversion rate. For example, oxidation of ethylene to ethylene oxide can be carried out over a silver-based catalyst (S. Rebsdat et al., U.S. Pat. Nos. 4,471,071 and 4,808,738). For a surface-supported catalyst with an area of 1 mm by 1 mm and the same activity as the industrial catalyst, only about 10 parts per billion (ppb) of ethylene are converted into the desired ethylene oxide when the contact time is one second.

Detection of such low component levels in the presence of several atmospheres of reaction mixture is a challenge to analytical methods. Many analytical techniques, including optical methods such as four-wave mixing spectroscopy and cavity ring-down absorption spectroscopy as well as conventional methods such as GC/MS, are excluded because of poor sensitivities, non-universal detectability, and/or slow response. Therefore an apparatus and methodology for screening a substrate having an array of materials that differ slightly in chemical composition concentration, stoichiometry, and/or thickness is desirable.

SUMMARY OF THE INVENTION

The present invention provides methods and apparatus for the rapid characterization and analysis of an array of materials using infrared imaging and spectroscopy techniques. Typically, each of the individual materials on the array will be screened or interrogated for the one or several material characteristics. Once screened, the individual materials may be ranked or otherwise compared relative to each other with respect to the material characteristic under investigation. Materials that can be compared using the methods and apparatus of the present invention include, for example liquids, dissolved organic or inorganic molecules, covalent network solids, ionic solids and molecular solids. In particular, the present invention is directed to characterization systems utilizing thermal imaging and infrared spectroscopic imaging.

According to one aspect of the present invention, infrared imaging techniques are used to identify the active compounds within an array of compounds by monitoring temperature change in the vicinity of the compound. Temperature change results from a reaction, either exothermic or endothermic in nature, and may be localized to specific compounds within the library as well as the region of the substrate adjacent to the compounds in question. This same technique can also be used to quantify the stability of each new material within an array of compounds by observing the temperature change as a function of time. By measuring the decay of activity through the change in temperature over time for each site, the lifetime of catalysts, for example, can be quantified.

According to another aspect of the invention, identification and characterization of the condensed solid or liquid phase products is achieved, wherein library elements are characterized by their specific infrared absorption or reflectance. Such materials may be the product of reactions, for example, in the gas phase polymerization of ethylene to condensed phase polyethylene or in the hydrolysis of liquid dimethyldichlorosilane to elastomeric polydimethylsiloxane. In one embodiment specific molecular vibrations are evaluated by measuring the IR absorption. Typically, the radiation from a monochromatic infrared source is passed through the library and the intensity of the transmitted beam is measured as a function of time during the progression of a reaction. In an alternate embodiment, the library is irradiated with polychromatic infrared radiation and an infrared bandpass filter is used to confine the detection to specific wavelength regions of the infrared spectrum.

In another aspect of the invention, heat transport properties are measured using the rate of heat dissipation in a library by observing the transient change in temperature of the library elements with infrared imaging. Preferably, a pulsed infrared source illuminates the back surface of the library while the front surface of the library is monitored. Thus a measure of the thermal conductivity of each of the elements can be easily obtained.

According to a further aspect of the invention, identification and characterization of material properties is achieved using a two-dimensional infrared imaging system. The imaging system simultaneously monitors each element of the library, wherein each individual library element's temperature as well as its difference relative to the surrounding elements reflects the activity and heat of reaction of the specific library site.

A further understanding of the nature and advantages of the inventions herein may be realized by reference to the remaining portions of the specification and the attached drawings.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Glossary

Figure 1:
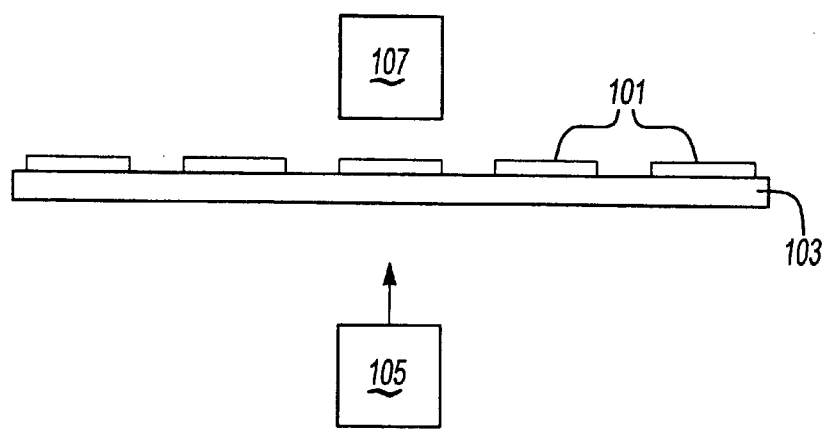
FIG. 1 illustrates an embodiment of the invention used to determine the relative thermal diffusivities of the different materials on a library.

The following terms are intended to have the following general meanings as used herein.

Substrate: A substrate is a material having a rigid or semi-rigid surface. In many embodiments at least one surface of the substrate will be substantially flat. In some embodiments the substrate will contain physical separations between synthesis regions for different materials. Suitable physical separations include, for example, dimples, wells, raised regions, and etched trenches. According to other embodiments, small beads or pellets may be provided on the surface, either alone or within substrate surface dimples. The surface area of the substrate is designed to meet the requirements of a particular application. Typically, the surface area of the substrate is in the range of 1 cm$^2$ to 400 cm$^2$. However, other sizes may be used with the present invention, for example surface areas as small as 0.001 cm$^2$ or as large as 10 m$^2$ are possible.

Predefined Region: A predefined region is a localized area on a substrate that is, was, or is intended to be used for the formation of a specific material. The predefined region may be referred to, in the alternative, as a "known" region, a "reaction" region, a "selected" region, or simply a "region." The predefined region may have any convenient shape, e.g., linear, circular, rectangular. elliptical, or wedge-shaped. Additionally, the predefined region can be a bead or pellet which is coated with the component(s) of interest. In this embodiment, the bead or pellet-can be identified with a tag, such as an etched binary bar code, that can be used to identify which components were deposited on the bead or pellet. The area of the predefined regions depends on the application and is typically smaller than about 25 cm$^2$. However, the predefined regions may be smaller than 10 cm$^2$, smaller than 5 cm$^2$, smaller than 1 cm$^2$, smaller than 1 mm$^2$, smaller than 0.5 mm$^2$, smaller than 10,000 $\mu$m$^2$, smaller than 1,000 $\mu$m$^2$, smaller than 100 $\mu$m$^2$, or even smaller than 10 $\mu$m$^2$.

Radiation: Radiation refers to energy with a wavelength between 10$^{-14}$ and 10$^4$. Examples of such radiation include electron beam radiation, gamma radiation, x-ray radiation, ultraviolet radiation, visible light, infrared radiation, microwave radiation, and radio waves. Irradiation refers to the application of radiation to a material or object.

Component: Component is used herein to refer to each of the individual substances that are deposited onto a substrate. Components can act upon one another to produce a particular material. Components can react directly with each other or with an external energy source such as radiation, an electric field, or a magnetic field. A third material or a chemical substance can also act upon components. A component can be an element, a chemical, a material, or a mixture of elements and chemicals. Components can form layers, blends or mixtures, or combinations thereof.

Source Material: The term source material is used herein to refer to the original material from which a component was derived. Source materials can be composed of elements, compounds, chemicals, molecules, etc. that are dissolved in a solvent, vaporized, evaporated, boiled, sublimed, ablated, etc., thus allowing the source materials to deposit onto a substrate during the synthesis process.

Resulting Material: The term resulting material is used herein to refer to the component or combination of components that have been deposited onto a predefined region of a substrate. The resulting materials may comprise a single component, or a combination of components that have reacted directly with each other or with an external source. Alternatively, the resulting material may comprise a layer, blend or mixture of components on a predefined region of the substrate. The resulting materials are screened for specific properties or characteristics to determine their relative performance.

Mixture or Blend: The term mixture or, interchangeably, blend refers to a collection of molecules, ions, electrons, or chemical substances. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

Layer: The term layer is used herein to refer to a material that separates one material, component, substrate or environment from another. A layer is often thin in relation to its area and covers the material beneath it. A layer may or may not be thin or flat, but once it is deposited it generally covers the entire surface such that it separates the component or substrate below the layer from the component or environment above the layer.

Heterogeneous catalysts: Heterogeneous catalysts enable catalytic reactions to occur with the reactants and catalysts residing in different phases. As used herein, heterogeneous catalysts include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts.

Homogeneous catalysts: Homogeneous catalysts enable catalytic reactions to occur with the reactants and catalysts residing in the same phase. As used herein, homogeneous catalysts include, but are not limited to, catalysts for the polymerization of one or more olefinic or vinyl monomers. The olefinic monomers include, but are not limited to, ethylene or alpha-olefins containing from 3 to 10 carbon atoms, such as propylene, 1-butene, 1-pentane, 1-hexene, and 1-octene. The vinyl monomers include, but are not limited to, vinyl chloride, vinyl acetate, vinyl acrylate, methylmethacrylate, methyl vinyl ether, ethyl vinyl ether and acetonitrile. The catalysts employed to carry out a polymerization of one or more monomers of this type include, but are not limited to, radical catalysts, cationic catalysts, anionic catalysts, and anionic coordination catalysts.

Generating Arrays of Materials

Generally, an array of materials is prepared by successively delivering components of the materials to predefined regions on a substrate, and simultaneously reacting the components to form at least two materials or, alternatively, the components are allowed to interact to form at least two materials. In one embodiment, for example, a first component of a first material is delivered to a first predefined location on a substrate, and a first component of a second material is delivered to a second predefined region on the same substrate. Simultaneously with or thereafter, a second component of the first material is delivered to the first region on the substrate, and a second component of the second material is delivered to the second region on the substrate. Each component can be delivered in either a uniform or gradient fashion to produce either a single stoichiometry or, alternatively, a large number of stoichiometries within a single predefined region. Moreover, the components can be delivered as amorphous films, epitaxial films or lattice or superlattice structures. The process is repeated, with additional components, to form a vast array of components at predefined locations on the substrate. Thereafter, the components are simultaneously reacted to form at least two materials or, alternatively, the components interact to form at least two materials. As described herein, the components can be sequentially or simultaneously delivered to the predefined regions on the substrate using any of a number of different delivery techniques.

Numerous combinatorial techniques can be used to synthesize the various arrays of diverse materials on the substrate according to the present invention. For example, in one embodiment a first component of a first and second material is delivered to the predefined regions on the substrate. Then a second component of the first and second materials is delivered to the predefined regions on the substrate. This process continues for the other components (e.g., third, fourth, fifth, etc. components) and/or the other materials (e.g., third, fourth, fifth, etc. materials) until the array is complete. In another embodiment, the array is formed as previously described, but the resulting materials are formed immediately as the components contact each other on the substrate.

In yet another embodiment, the array is formed as previously described, but after the various components are delivered to the substrate, a processing step is carried out which allows or causes the components to interact to form layers, blends, mixtures, and/or materials resulting from a reaction between components. In still another embodiment, two or more components are delivered to the predefined regions on the substrate using fast sequential or parallel delivery techniques such that the components interact with each other before contacting the substrate. The resulting array of materials, each at a discrete and known location on the substrate, comprises layers, blends, mixtures, and/or materials resulting from a reaction between components.

Essentially, any conceivable substrate can be employed in the invention. The substrate can be organic, inorganic, biological, nonbiological, or a combination thereof. The substrate can exist as particles, strands, precipitates, gels, sheets, tubing, spheres, containers, capillaries, pads, slices, films, plates, slides, etc. The substrate can have any convenient shape, such as a disc, square, sphere, circle, etc. The substrate is preferably flat, but may take on a variety of alternative surface configurations. For example, the substrate may contain raised or depressed regions on which the synthesis of diverse materials takes place. The substrate and its surface preferably form a rigid support on which to carry out the reactions described herein. The substrate may be any of a wide variety of materials including, for example, polymers, plastics, pyrex, quartz, resins, silicon, silica or silica-based materials, carbon, metals, inorganic glasses, inorganic crystals, and membranes. Upon review of this disclosure, other substrate materials will be readily apparent to those of skill in the art. Surfaces on the solid substrate can be composed of the same materials as the substrate or, alternatively, they can be different (i.e., the substrates can be coated with a different material). Moreover, the substrate surface can contain thereon an adsorbent (for example, cellulose) to which the components of interest are delivered. The most appropriate substrate and substrate-surface materials will depend on the class of materials to be synthesized and the selection in any given case will be readily apparent to those of skill in the art. In other embodiments, the substrate can be a series of small beads or pellets. As with the single substrate having an array of materials thereon, each of the individual beads or pellets can be screened for materials having useful properties.

A variety of substrate systems are possible, including two- and three-dimensional substrate systems. In some embodiments, the two-dimensional combinatorial catalysis library will be deposited either on a porous substrate, such as alumina, or on a non-porous substrate. In some embodiments, the substrate will further contain a synthesis support. The synthesis support can be made of alumina, silicon, quartz, zeolites, Teflon, silica and other oxides, etc. The synthesis support may be in the form of beads, discs or any other geometry in, for example, one of the following substrate configurations: i) a porous support placed in wells wherein the reactants flow through the support from the top of the wells out through a hole in the bottom of the wells (or flow may be in the reverse direction); ii) a porous support placed in wells wherein the reactants do not flow through from the top to the bottom of the wells, but only to and from the top of the wells; iii) a non-porous support placed in wells wherein the reactants flow around the support from the top of the wells out through a hole in the bottom of the wells (or flow may be in the reverse direction); iv) a non-porous support placed in wells wherein the reactants do not flow through from the top to the bottom of the wells, but only to and from the top of the wells; or v) a porous or non-porous support not contained in wells wherein the reactants are deposited directly onto the substrate surface.

Generally, physical masking systems can be employed in combination with various deposition techniques in order to apply components onto a substrate in a combinatorial fashion, thereby creating arrays of resulting materials at predefined locations on the substrate. The arrays of resulting materials will usually differ in composition, stoichiometry and/or thickness across the substrate. The components can, for example, be dispensed to the substrate in the form of a gas, a liquid or a powder. Suitable deposition techniques include, but are not limited to, sputtering, electron-beam and thermal evaporation, laser deposition, ion beam deposition, chemical vapor deposition, and spray-coating. In solution phase deposition techniques include, for example, sol/gel methods, discrete liquid dispensing techniques (e.g. pipettes, syringes, ink jets, etc.), spin coating with lithography, microcontact printing, spraying with masks and immersion impregnation. Moreover, such dispenser systems can be manual or, alternatively, they can be automated using, for example, robotics techniques. A more complete description of representative arrays of materials and systems and methods for generating such arrays of materials can be found in commonly assigned, co-pending patent applications "The Combinatorial Synthesis Of Novel Materials", Publication No. WO 95/13278, filed Oct. 18, 1995; "Systems and Methods for the Combinatorial Synthesis of Novel Materials," patent application Ser. No. 08/841,423, filed Apr. 22, 1997; and "Discovery of Phosphor Materials Using Combinatorial Synthesis Techniques," provisional patent application Ser. No. 60/039,882, filed Mar. 4, 1997; the complete disclosures of which are incorporated herein by reference for all purposes.

In some embodiments of the present invention, after the components have been deposited onto predefined regions on a substrate, they are reacted using a number of different techniques. For example, the components can be reacted using solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent, etc. Furthermore, each predefined region on the substrate can be heated simultaneously or sequentially using heat sources such as focussed infrared radiation, resistive heating, etc. Reactants can, for example, be dispensed to the library of elements in the form of a gas or a liquid. Other useful techniques that can be used to react the components of interest will be readily apparent to those of skill in the art. Additionally, components can react with each other instantly, upon contacting each other, or in the air before contacting the substrate. The components can also form layers, blends or mixtures, in the air or on the substrate, rather than reacting with each other.

Once prepared, the array of resulting materials can be screened for useful properties using the methods described herein. Either the entire array or, alternatively, a section thereof (e.g., a row of predefined regions) can be screened using parallel or fast sequential screening. In some embodiments, a predefined region on the substrate and, therefore, the area upon which each distinct material is synthesized, is smaller than about 25 cm$^2$, less than 10 cm$^2$, less than 5 cm$^2$, less than 1 cm$^2$, less than 1 mm$^2$, or less than 0.5 mm$^2$. In other embodiments, the regions have an area less than about 10,000 $\mu$m$^2$, less than 1,000 $\mu$m$^2$, less than 100 $\mu$m$^2$, or less than 10 $\mu$m$^2$. Accordingly, the density of regions per unit area will be greater than 0.04 regions/cm$^2$, greater than 0.1 regions/cm$^2$, greater than 1 region/cm$^2$, greater than 10 regions/cm$^2$, or greater than 100 regions/cm$^2$. In other embodiments, the density of regions per unit area will be greater than 1,000 regions/cm$^2$, greater than 10,000 regions/cm$^2$, greater than 100,000 regions/cm$^2$, or greater than 10,000,000 regions/cm$^2$.

In some embodiments, the screening systems of the present invention will be used to screen a single substrate having at least 9 different materials. In other embodiments, the screening system scans a single substrate having more than 50, 100, 10$^3$, 10$^4$, 10$^5$, 10$^6$, or more materials synthesized thereon. In some embodiments, the substrate will comprise arrays of materials with as few as two components, although the substrate can have materials with 3, 4, 5, 6, 7, 8 or more components therein. The substrate can be screened for materials having useful properties and/or the resulting materials can be ranked, or otherwise compared, for relative performance with respect to useful properties or other characteristics. Resulting materials include, but are not limited to, covalent network solids, ionic solids and molecular, inorganic materials, intermetallic materials, metal alloys, ceramic materials, organic materials, organometallic materials, nonbiological organic polymers, composite materials (e.g., inorganic composites, organic composites, or combinations thereof), or homogeneous or heterogeneous catalysts. Again, once useful resulting materials have been identified using the methods of the present invention, a variety of different methods can be used to prepare such materials on a large or bulk scale with essentially the same structure and properties. Properties which can be screened for include, but are not limited to, electrical, thermal, mechanical, morphological, optical, magnetic, chemical, conductivity, super-conductivity, resistivity, thermal conductivity, anisotropy, hardness, crystallinity, optical transparency, magnetoresistance, permeability, frequency doubling, photoemission, coercivity, dielectric strength, or other useful properties which will be apparent to those of skill in the art upon review of this disclosure. Importantly, the synthesizing and screening of a diverse array of resulting materials enables new compositions with new physical properties to be identified.

Given the chemical complexity of catalytic systems, the lack of predictive models, the number of possible combinations of metals, counterions, ligands, and supports, and the time consuming process of evaluating the performance of each catalyst formulation utilizing conventional laboratory pilot reactors, it is not surprising that the search for the optimum catalyst is a time consuming and inefficient process. Thus, a combinatorial approach to the discovery and optimization of catalytic systems, which combines the synthesis of catalyst libraries with the screening tools of this invention, is useful for accelerating the pace of research in this field. The catalyst libraries of the present invention can include organic (e.g., catalytic antibodies), organometallic, heterogeneous or solid state inorganic array elements. Organometallic catalyst libraries which can be screened for useful catalytic properties include, but are not limited to, those described in co-pending U.S. patent application Ser. No. 08/898,715, filed Jul. 22, 1997, which is hereby incorporated by reference for all purposes.

Catalyst libraries comprising inorganic (e.g., heterogeneous and solid state inorganic) materials can also be screened for useful properties using the methods of this invention. Catalyst libraries can comprise powders, impregnated solid supports, inorganic films and monoliths, or crystals that are spatially separated within a substrate system (e.g., wells, flat surfaces). Solid state inorganic materials useful as heterogeneous catalysts are well known in the chemical industry. Heterogeneous catalysts enable catalytic reactions to occur with the reactants and catalysts residing in different phases and include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts. Heterogeneous catalyst systems typically comprise metals, metal oxides, metal sulfides, and other metal salts, can be supported on a carrier (e.g., alumina, silica of controlled particle size and porosity), and can be used in bulk.

Heterogeneous catalysts can be prepared by a number of methods which are well known in the art and include mixing reactive solutions, impregnation of solutions of metal salt precursors onto or into solid carriers, coprecipitation, and mixing colloidal dispersions. These methods yield chemically complex, multicomponent solid products that can be further treated with reducing agents, oxidizing agents and other third components and modifiers to produce optimized materials.

Once an array of catalysts is formed, the screening methods of the present invention can be used to characterize the catalytic properties of the various compounds by observing, for example, activity, lifetime and selectivity for a variety of catalytic transformations. For purposes of this invention, a catalyst is defined as any material that accelerates the rate of a chemical reaction and which is either not consumed during the reaction or which is consumed at a rate slower (on a molar basis) than the reaction that is being catalyzed. Examples of catalytic reactions/transformations include, but are not limited to, total oxidations (e.g., the conversion of CO into $CO_2$ using oxygen, or $NO_x$ for simultaneous reduction of the $NO_x$), selective oxidations (e.g., epoxidations of olefins), reductions (e.g., hyrdogenation of unsaturated species), polymerizations (e.g., ethylene copolymerizations), dimerization (e.g., ethylene to butene), trimerization, oligomerization, decompositions (e.g., conversion of $NO_x$ into $N_2$ and $O_2$), hydrosilation, carbonylations, hydrocynation, hydroformylation, isomerization, metathesis (e.g., of olefins and acetylenes), carbon-hydrogen activation, cross coupling, Friedel-Crafts acylation and alkylation, hydration, and Diels-Alder reactions.

Thermal Imaging of Combinatorial Libraries

The thermodynamic evaluation of combinatorial chemical libraries provides critical information useful in the discovery and optimization of new materials.

Thermodynamic characterization relates the observable bulk properties of a material (volume, enthalpy, heat capacity, free energy, heat of reaction, catalytic activity, thermal conductivity, etc.) to imposed external conditions (pressure, temperature, composition, etc.). In principle, thermodynamic measurements are taken and the results tabulated and used to monitor trends in the observed systems under different conditions.

The temperature of an entire library of materials may be monitored with an infrared camera as a measure of the thermodynamic quantities associated with the materials, the measurements performed either serially or in parallel. Commercial position sensitive systems such as infrared focal plane arrays, for example comprised of InSb or HgCdTe detectors, have a sensitivity of better than ±0.05°C. over the range of temperatures from −50° C. to 800°C. and a spatial resolution of better than 1 mm depending on the optics. The speed of the data acquisition from a commercial infrared camera is as high as 120 frames per second, thus providing sufficient speed to follow most chemical reactions and thermal diffusion transients.

In a specific embodiment, the infrared camera is used to monitor the heats of reaction of a combinatorial library under various external conditions such as temperature and gas flow. For example, if a solid catalyst library and its surrounding support in a two-dimensional library are exposed to a reactant, a measurable heating of the surroundings may occur depending on the activity of the chemical process. In the case of a catalyst, the activity of the catalyst on the support will be represented through the energy released or absorbed as heat during the chemical reaction between the catalyst and the exchange gas. In a combinatorial library, elements are nearly identical in thermal mass such that measurements of the heat evolved by one element in the library relative to others within the library reveals trends useful in the characterization of the chemical processes induced by these materials.

According to another embodiment of the invention illustrated in FIG. 1, the relative thermal diffusivities of the different materials on a library are measured, thus providing a measure of the material density, thermal conductivity, and specific heat for the individual materials. The different materials 101 are affixed to a uniform substrate 103, for example using a deposition process. A modulated heat source 105 is directed toward the underside of the library, either directly adjacent to a single element or in such a manner as to simultaneously and uniformly irradiate the entire library. An IR detector 107 scans the library, either by repositioning the detector or by repositioning the library relative to the detector. Detector 107 monitors the temperature change of library materials 101 in response to the modulation of heat source 105. If heat source 105 does not simultaneously and uniformly irradiate the entire library, it must be scanned in conjunction with detector 107, thus insuring that the monitored thermal diffusivities correspond to the same heat input. To maximize the sensitivity of this configuration, substrate 103 should be as thin and thermally transparent as possible.

Figure 2:
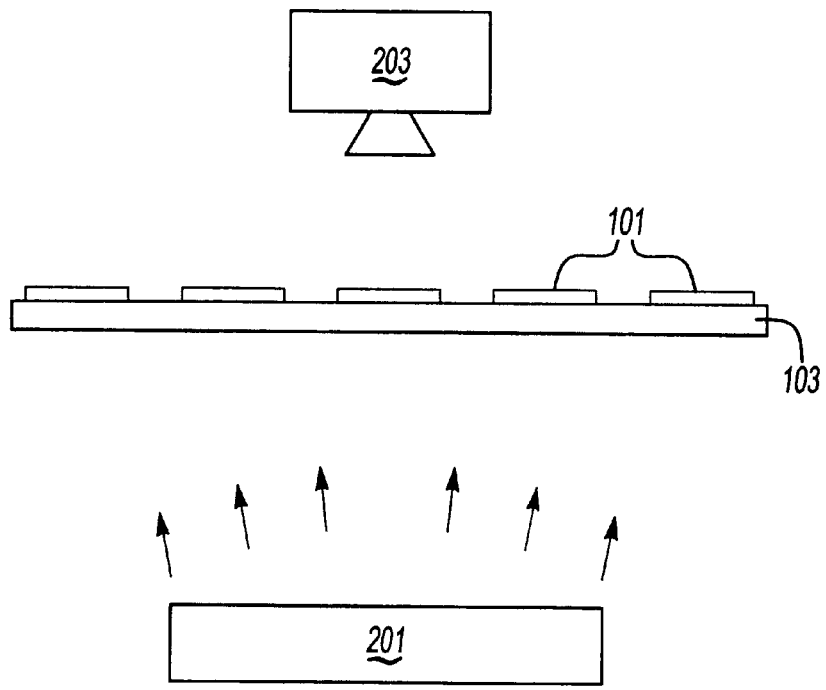
FIG. 2 illustrates a non-scanning configuration of the embodiment shown in FIG. 1.

FIG. 2 illustrates a second configuration of the embodiment shown in FIG. 1.

In this configuration, a modulated heat source 201 simultaneously and uniformly irradiates the entire substrate 103, and thus all library materials 101. A position sensitive IR detector array 203 monitors the temperature change of all library elements 101, thus removing the necessity for a translation system.

Figure 3:
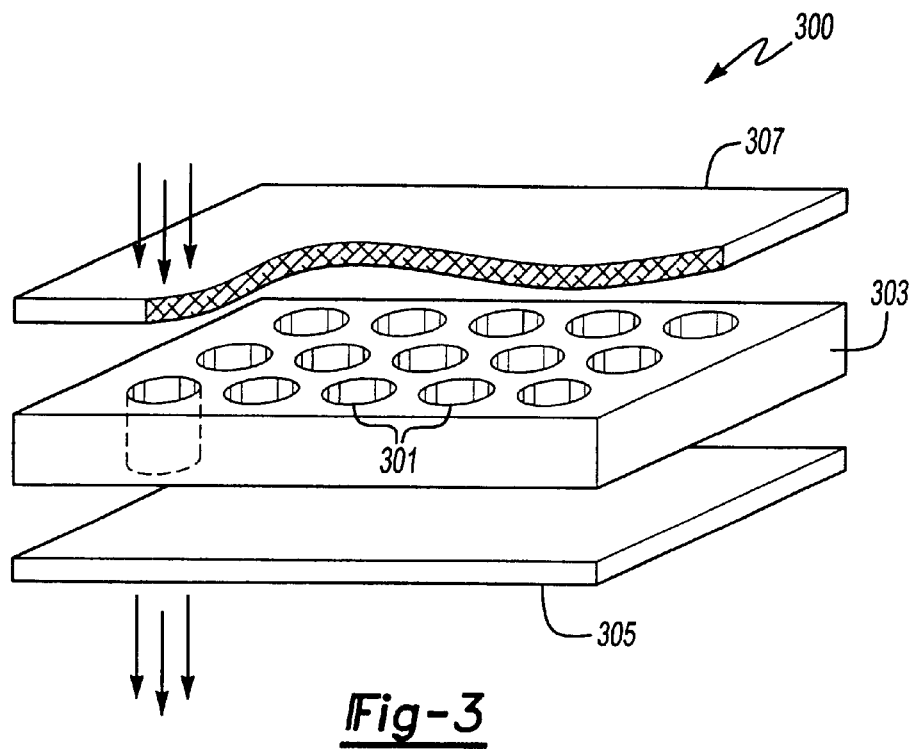
FIG. 3 depicts a two-dimensional library of materials within wells on a substrate according to the invention.

FIG. 3 illustrates a two-dimensional library 300 of materials according to one embodiment of the invention. The individual library elements are contained within a plurality of reaction wells 301 in a substrate 303. Substrate 303 is placed within a sealed reaction chamber (not shown) which is subsequently filled with selected gases and pressurized. Substrate 303 is then heated in situ. Windows 305 and 307 are made of an infrared transparent medium (e.g., $BaF_2$, $CaF_2$, NaCl, etc.) capable of holding the pressurized gas inside the chamber. Since windows 305 and 307 are transparent, thermal imaging techniques can be used to monitor, in parallel, the heat of reaction of the array under various external conditions.

Measuring the heat of reaction through temperature changes is a useful technique for screening catalytic rate. Though insensitive to products, this method provides a parallel, high-throughput screen when activity is of interest. For condensed phase products of both homogeneous and heterogeneous catalysis, the products themselves are in thermal contact with the catalyst. Thus, infrared emission imaging of the library elements provides a unique means of screening large libraries in parallel. If large differences in emissivity are observed for the individual library elements, an alternate embodiment may be used in which the imaging is performed from the side of the substrate opposite the library elements. In this configuration the imaging is performed through a material, such as graphite, having a uniform emissivity. As a result, a significantly better signal to noise ratio is achieved. However, since relative changes in temperature are of interest, emissivity differences do not preclude the usefulness of the measurement.

In the condensed phase detection system described above, the products, catalyst and support will all change temperature. However, in the gas phase the temperature variation is limited to the catalyst and support. The temperature of each individual library element as well as the difference in temperature relative to the surrounding elements reflects the activity of a specific library site and the heat of reaction. Preferably the catalyst support has minimal thermal mass and the catalyst surface area for each library element is nearly identical.

In order to perform a measurement, the sample chamber, library, and structure is first equilibrated to a uniform temperature. An inert gas fills the chamber at a pre-defined pressure. At a time t equals 0, the desired reactant gas is leaked into the chamber and the substrate temperature is monitored. Preferably the substrate temperature is monitored at periodic intervals although continuous monitoring may also be used. The rise or fall in temperature of the thermal mass supporting the catalyst is a direct measure of the exothermic or endothermic catalytic activity of the site.

As an estimate of the temperature change expected, if a microjoule is deposited in a 1 mm×1 mm×0.0001 mm region of material, a temperature change of approximately 0.5 K is expected. The reaction of ethylene and hydrogen to ethane produces 120 KJ/mole and, therefore, 1 microjoule requires only the reaction of $5 \times 10^{12}$ molecules. Many times that number of molecules will react per second on a typical 1 mm×1 mm×0.0001 mm porous support or on a non-porous 1 mm×1 mm×0.000001 mm film. In another embodiment, individual elements can be monitored in series using position insensitive temperature detection technology or single element scanned detectors.

EXAMPLE

Figure 4:
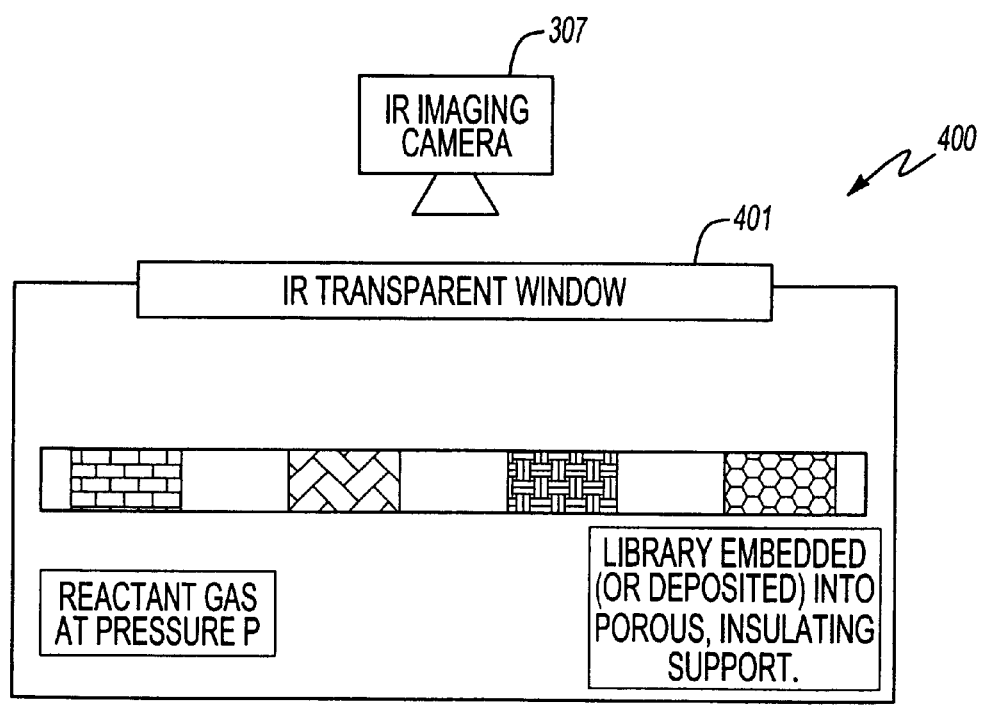
FIG. 4 depicts a reaction chamber for monitoring thermal emission of a polymerization reaction at a predefined pressure and temperature.
Figure 5:
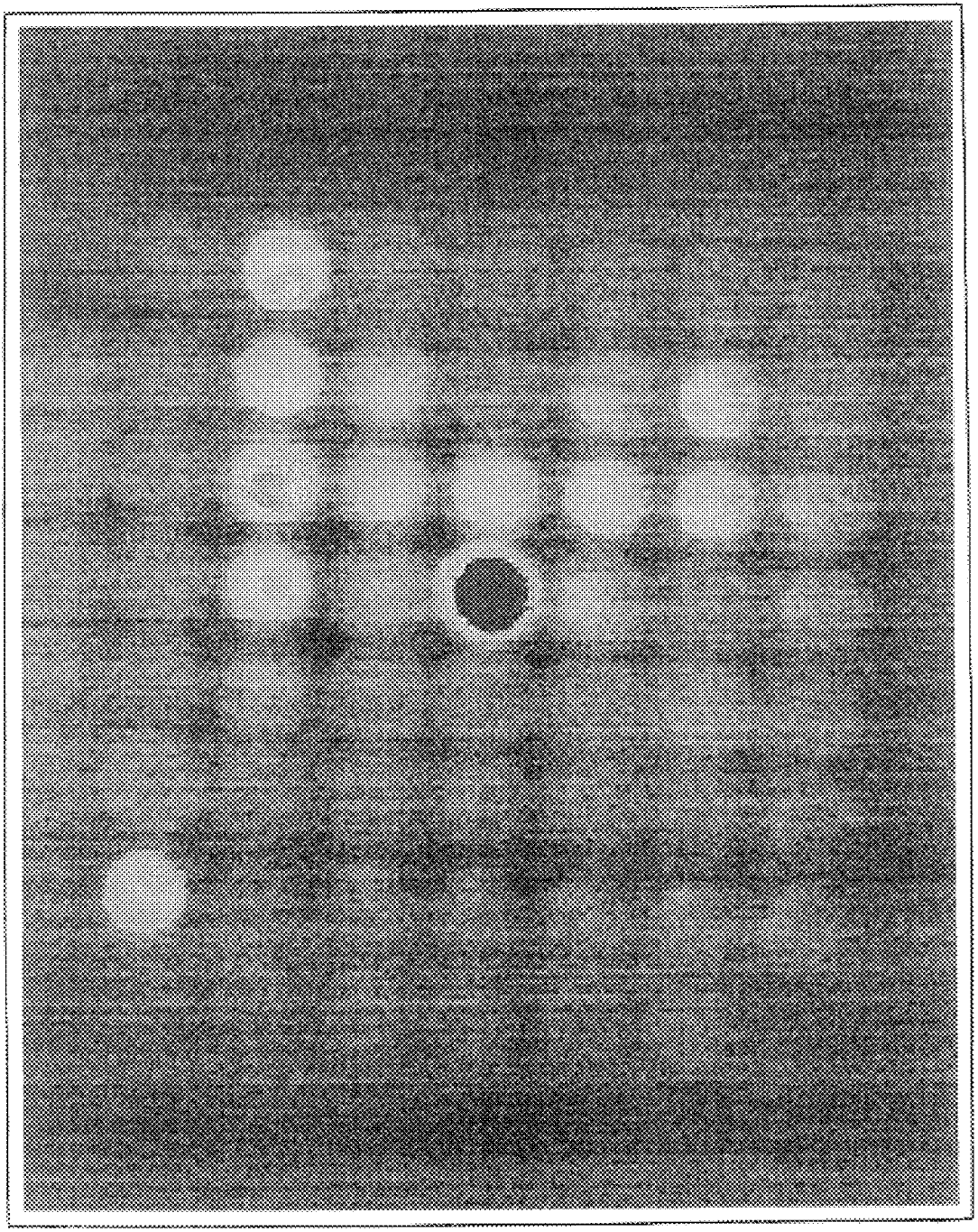
FIG. 5 depicts a thermal map of a polymerization reaction for 61 elements in a library of elements within a pressurized reaction chamber.

The following example indicates the use of thermal imaging according to the invention to monitor thermal emission during a polymerization reaction. FIG. 4 illustrates a reaction chamber 400 for monitoring thermal (i.e., infrared) emission at a predefined pressure and temperature. Thus system 400 can be used to screen libraries of potential catalysts for activity under polymerization conditions. Typically a library of catalysts, such as the substrate shown in FIG. 3, is placed in system 400. The catalysts, solvents, initiators, and additional components necessary to carry out the polymerization reaction are placed into wells within thermostatted substrate 303, which is capable of reaching elevated temperatures, such as 100° C., under an overpressure of gas, such as ethylene gas at 40 psig. The temperature of each well is monitored through an IR transparent window 401 with a position sensitive imaging system 403. Preferably imaging system 403 captures thermal maps of the library at fixed intervals in time. FIG. 5 illustrates a representative thermal map 500. The library imaged in thermal map 500 includes 61 elements. As illustrated, higher temperatures are indicated by an increase in image intensity as well as a change in color from blue to red.

Figure 6:
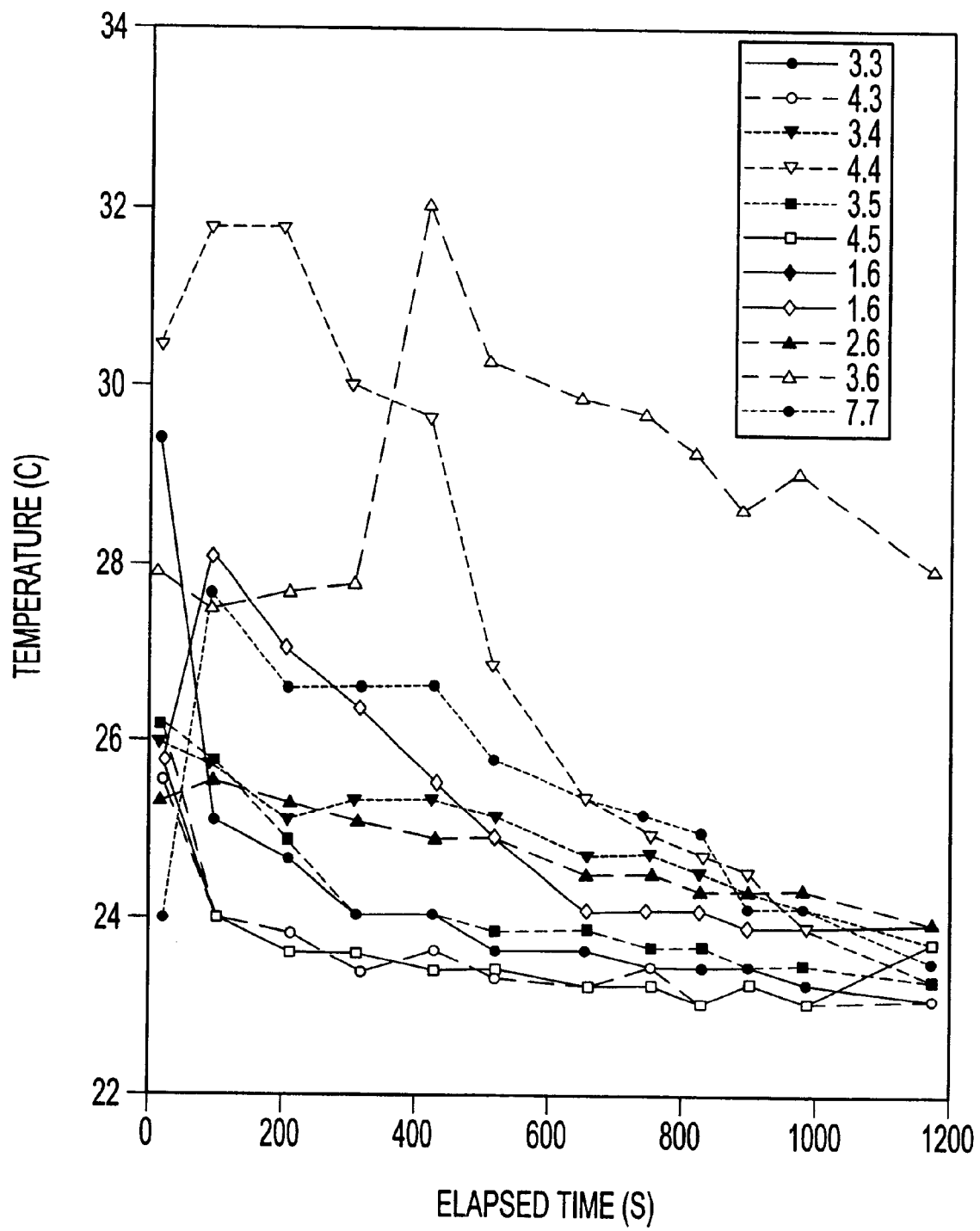
FIG. 6 graphically illustrates the thermal evolution as a function of time for the polymerization reactions of eleven wells of a library.

The graph illustrated in FIG. 6 provides the temperature of eleven representative library elements as a function of time. If higher resolution is required, more frequent data points can be obtained simply by decreasing the time intervals between IR images.

Differential Thermal Analysis

Changes in the structure and bonding of a chemical composition during a transition from one thermodynamically stable phase to another results in heat being evolved (exothermic process) or absorbed (endothermic process). Therefore during a phase transition the temperature of the sample of interest may change or the rate of temperature change may increase or decrease. Traditionally, differential thermal analysis is performed in a sealed environment where the temperature of the material being measured is compared to the temperature of a standard material (e.g., $\alpha$-$Al_2O_3$) having no phase transition as the temperature is varied over the range of interest. In differential thermal analysis, the temperature of the standard material is subtracted from the temperature of the sample material to yield the temperature difference. Then a graph is made of the temperature versus the derived temperature difference.

In another embodiment of the invention differential thermal analysis of combinatorial libraries is performed using an infrared camera. The infrared camera monitors the temperature of every library element in parallel and compares it to the temperature of a known standard material deposited within the field of view of the camera and subjected to the same physical conditions as the library elements. In this way, complicated phase relationships are measured for large libraries of materials by heating or cooling the library and measuring changes in the differential temperature or in the slope of the differential temperature versus the actual temperature.

Rapid Screening of Combinatorial Libraries with Infrared Spectroscopy

Until now there has been no known device capable of characterizing in parallel the structure activity relationships for a large number of chemical reactions on a time scale relevant to the speed of most polymerization and catalytic reactions. Most existing instruments characterize one sample at a time, or a number of samples in series at a rate that is slower than most chemical reactions.

The present invention provides a system for simultaneously characterizing the reaction products from a library of different catalysts. In one example, the products are polymers and information about polymer structure may be obtained. Preferably the system operates in the near-IR (NIR) (12,500–4000 $cm^{-1}$) and mid-IR regions (4000 –200 $cm^{-1}$) of the spectrum.

Absorption bands in the near-IR region are caused by overtones and combinations of fundamental molecular vibration bands commonly found in the mid-IR. Thus the near-IR region is a somewhat simpler spectrum for a computer to fit analytically. In general, the relationship between changes in the absorption spectrum and changes in the physical properties of the polymers is determined empirically with the aid of a computerized fit of the near-IR spectrum. The relative nature of the absorption analysis in the near-IR makes it suitable for high-throughput screening. Polymer molecular weight, melt index, tacticity, branching ratio, and the degree of conversion are examples of information that can be obtained from analysis of the near-IR spectrum.

The mid-IR region of the spectrum provides much more information about the vibrational character of polymers. For example, structural parameters such as the frequency of methyl, butyl, and ethyl branches in polyethylene can be determined from changes in the peak absorbances in the mid-IR region.

There are several configurations of the invention that can be used to measure the infrared absorption spectrum of a combinatorial library, examples of which are described below.

Infrared Absorption Spectroscopy Using a Monochromatic Source

According to one embodiment of the invention, specific molecular vibrations are evaluated by infrared absorption. Because C=C stretch modes have specific absorptions at 1650 and 2200 $cm^{-1}$, monitoring the relative change in absorption at those frequencies over a library provides a measure of the relative change in the number of C=C bonds in the system. Therefore, the change in absorption reflects structural changes that occur during polymerization, for example during the polymerization of ethylene.

Figure 7:
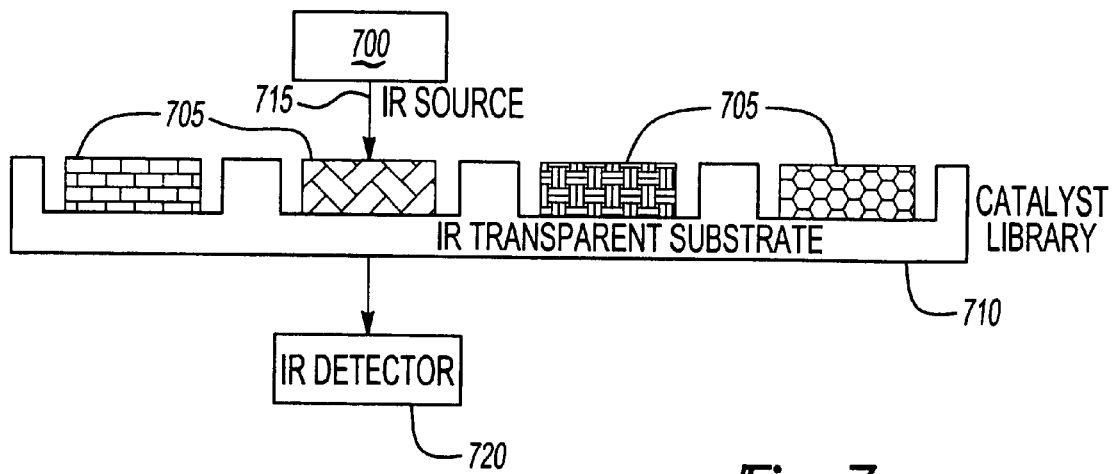
FIG. 7 depicts an infrared source irradiating a library of compounds on an infrared transparent substrate according to the invention.

FIG. 7 illustrates a system in which a monochromatic infrared source 700 irradiates a library of compounds 705 contained on a substrate 710. Substrate 710 is made of an infrared transparent material such as $BaF_2$, $CaF_2$, or NaCl, and may or may not include wells, as shown. Source 700 can be a monochromatic infrared source tuned to a specific wavelength using selective filters, for example, or any other tunable monochromatic source. The intensity of the portion of IR beam 715 passing through library element 705 and substrate 710 is detected as a function of time by an IR sensor 720. IR sensor 720 may be comprised, for example, of either HgCdTe or InSb detectors. By monitoring the infrared absorption as a function of time, the progression of the reaction can be monitored.

Source 700 can be directed through individual library elements one-by-one in a serial fashion, or a large area source beam can be passed through the entire library.

Similarly, infrared detection system 720 may be a single infrared detector scanned over the library in a serial manner, or it may be a position sensitive imaging system monitoring the absorption of all of the library elements in a parallel manner.

Infrared Absorption Spectroscopy using a Polychromatic Source

Figure 8:
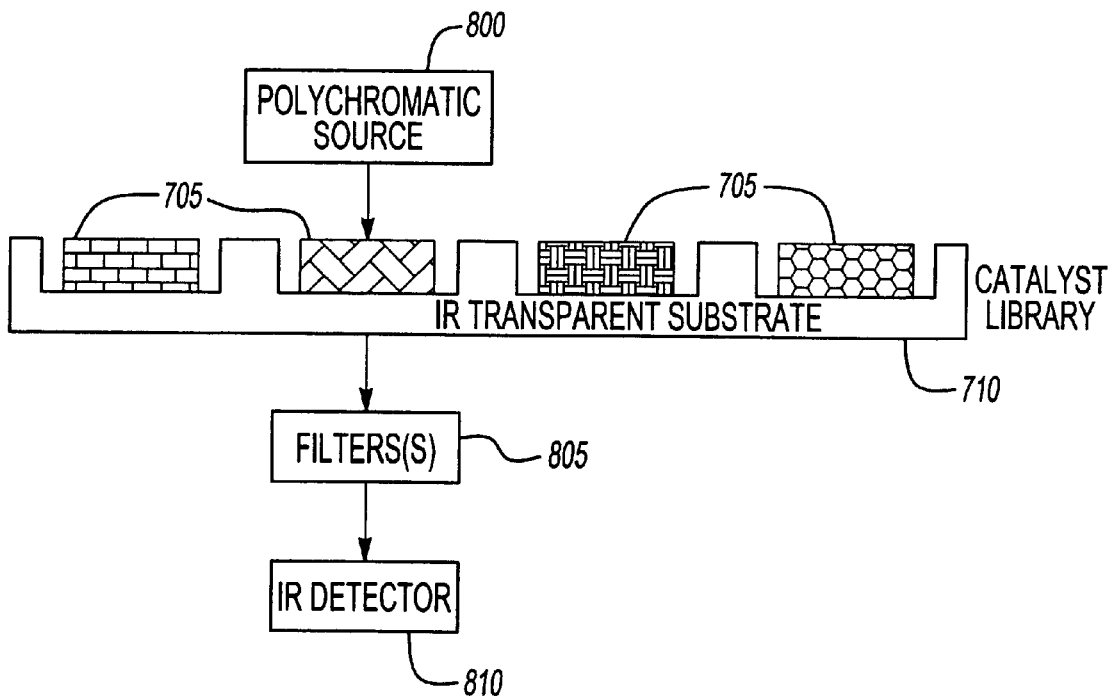
FIG. 8 depicts a polychromatic source irradiating a library of compounds on an infrared transparent substrate according to the invention.

According to another embodiment of the invention, the absorption of specific molecular vibrations in the infrared is measured after irradiating a library with polychromatic radiation. After absorption by the library, the radiation passing through the library elements is filtered so as to detect a desired wavelength region using selective bandpass filters. FIG. 8 illustrates a system using a polychromatic source 800 to irradiate a library of compounds 705 on infrared transparent substrate 710. In this embodiment, one or more filters 805 are placed between the library and the detector system 810. As in the above example, the system can use either a broad area beam to irradiate the entire library or a smaller beam can be used to irradiate some subset of library elements, for example a single element. Similarly, filters 805 and detection system 810 can scan over the library in a serial fashion, or the entire library can be monitored using a position sensitive detector. Filters 805 can be either separate from, or integral with, detection system 810.

Infrared Absorption Spectroscopy using an FT-IR Imaging System

In another embodiment of the invention, a large number of chemical reactions can be characterized on a time scale of minutes rather than hours. The system generally includes a Fourier transform infrared (FT-IR) spectrometer, a high-speed infrared camera, and a computer. In an embodiment configured for operating in a transmission mode, a modified FT-IR spectrometer generates a modulated infrared beam of radiation that is focused onto the combinatorial library where it interacts with the compounds of interest. After interaction with the library, the beam is re-focused onto the focal plane array (FPA) of a high-speed infrared camera. The FPA acts as an area detector to capture radiation for every position within the field of view, allowing for true parallel detection of the IR spectra for large combinatorial libraries.

Figure 9:
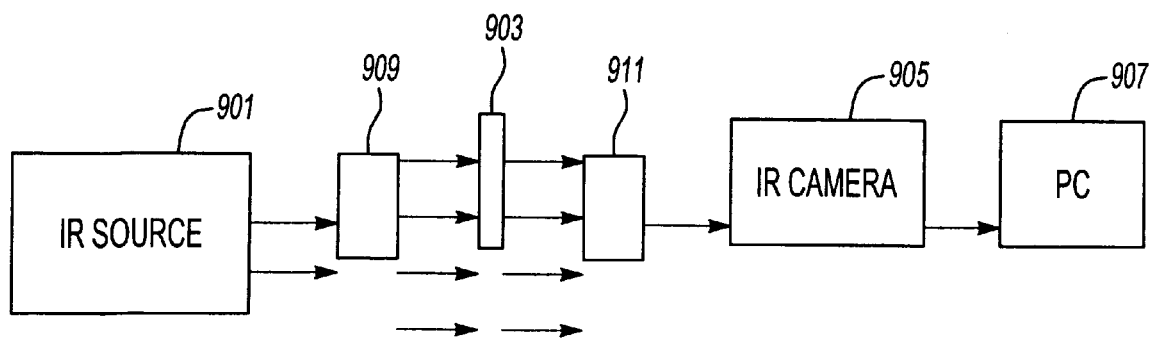
FIG. 9 depicts a schematic of an IR imaging system according to the invention.

FIG. 9 schematically illustrates an IR imaging system according to the present invention. The system includes an IR source/interferometer 901, a sample/library region 903 and an infrared camera 905 coupled to a computer 907. The system requires a sufficiently intense source of modulated IR radiation to uniformly illuminate the extended sample region of interest. Interferometer 901 modulates the signal frequency into a range detectable by camera 905. After leaving interferometer 901, the IR beam is expanded, for example using lens 909, prior to interacting with sample 903. Suitable collection optics 911 focuses the IR beam passing through sample 903 onto the FPA of camera 905. Infrared camera 905 captures position sensitive infrared profiles sequentially in time at a rate determined by the desired spectral resolution and spectral bandwidth, preferably at a rate of 60 frames/sec or greater. The sequential intensity profiles are transformed (using Fourier analysis) into a complete infrared spectrum with the aid of computer 907.

Infrared source 901 of the imaging FT-IR setup generally includes a radiation source and signal processing equipment (e.g., interferometer). A typical source is a glowbar or some other heated material capable of producing a polychromatic spectrum covering the infrared region of interest.

In an FT-IR system, light from a point source is rendered parallel by a collimator and passed on to a beamsplitter. The two beams formed by the beamsplitter travel to the mirrors and are reflected back. The beams then recombine at the beamsplitter where they interfere to produce an interferogram that is directed at the combinatorial library. After interacting with the library, the infrared radiation passing through the library is focused onto the detector. The detector records an intensity signal that depends on the path difference imposed by the travel to and from the mirrors and the absorption by the materials in the combinatorial library. The distance from the beamsplitter to the mirrors is arbitrary; what matters is the difference in the lengths of the paths.

One of the mirror arms in the interferometer is moved at a constant velocity, V. When illuminated by a monochromatic source, the detector will see a periodically varying cosine wave. The electrical frequency f of this wave is determined by the rate of change of the path difference dD/dt. Since dD/dt is simply 2V, f is equivalent to 2nV. Therefore, a Michelson interferometer can be considered to be a form of frequency transducer that converts optical frequencies which are typically too fast for a detector to monitor down to electrical frequencies that can have any value determined by the mirror velocity V.

The path difference is easily determined with the aid of a laser, for example a HeNe laser. The laser beam is sent through the interferometer concurrently with the IR radiation. As the path difference changes, the monochromatic laser light forms a cosine wave at a detector. By counting the number of maxima (fringes) in the pattern generated by the recombined beam, the path difference can be measured very precisely, as is well known in the art.

There are two fundamentally different approaches to the control of a FT-IR spectrometer. In the first, the mirror is moved at a constant velocity, resulting in a continuous output at the detector. Most commercial FT-IR spectrometers use an interferometer that has continuous scanning of the interferometer mirror. In the second approach, the mirror is stepped between sample points as quickly as possible. At each step, the mirror is held in position for the desired integration time. This approach, known as step scanning, has two distinct advantages over continuous scanning. First, measuring the mirror position and therefore the path difference is easier and more precise. Second, in the preferred embodiment the imaging system relies on an infrared camera with a FPA of roughly 256×256 (65,536) elements. Due to the size of the FPA, the rate at which data can be unloaded from the array is limited. Step scanning allows for a slight pause as the mirror steps to the next position during which the data can be unloaded from the FPA. A triggering signal is provided to the IR camera when the mirror reaches a given position. The obvious drawback of a step scanning interferometer relative to a continuous scanning interferometer is the speed at which data can be obtained.

Commercial step scanning interferometers operating in the mid-IR typically use a glowbar source capable of producing a power density of 0.7 mW/mm$^2$(i.e., 35 mW over an 8 mm diameter beam). Therefore, expansion of the standard beam over the full size of a polymer library requires increasing the power output of the source to maintain the same power density across each element in the library. For example, illuminating a 40 mm diameter area at 0.7 mW/mm$^2$ requires a glowbar power of 880 mW, a factor of 25 greater than a typical glowbar. Furthermore, as the power output of the source is increased, the power handling capabilities of the interferometer optics must be similarly increased. One approach for a high intensity source is to utilize multiple glowbar sources with an appropriate ellipsoidal mirror. The intensified beam is then collimated.

Expansion optics 909 should be capable of expanding the high intensity beam from the interferometer without an appreciable power loss. This is possible with laser-beam expanders that have IR transmission coatings optimized for the spectral range of the FPA. If desired, fiber optics can be used to confine the radiation to the reaction wells, therefore reducing the total power required by eliminating the power that is normally wasted on the dead space between the reaction wells.

According to the present invention, the spectroscopic imaging system provides parallel measurement of the infrared spectrum of a combinatorial library of compounds. Therefore, the modulated IR radiation from the interferometer preferably interacts with each sample in the library before it reaches the IR camera. There are two different sample configurations that are useful far polymer analysis: (i) post polymerization analysis of polymer films that can be void of solvent and (ii) in situ analysis of polymerization reactions where solvent may be present. Both configurations can be performed with transmission spectroscopy. However, the restraints on the samples differ for each configuration due to the detection limits of the FPA and interactions with the solvent.

Post reaction analysis of thin-film libraries is significantly easier than the in situ analysis. Aside from eliminating the solvent peaks from the spectrum, the signal to noise ratio is maximized by increasing the integration time on the FPA since the time constraints placed on the system while attempting to track a chemical reaction are eliminated. The signal to noise ratio is further maximized due to the inherent increase in absorption resulting from a high concentration of polymer interacting with the source radiation. A thin-film library can be robotically deposited on a suitable IR transmitting substrate and then imaged in parallel very easily with this system.

Monitoring a polymerization reaction is substantially more complicated. First, a reaction vessel capable of holding the polymer solutions must be constructed with the following criteria: (i) at least one side of the reaction vessel must have an IR transparent material to allow the radiation to pass through the sample; (ii) the general features of a polymerization reactor must be maintained (e.g. temperature control, mixing/agitation, etc.); and (iii) the thickness and therefore the IR path length of the reaction vessel must be small enough that the radiation is not completely attenuated, but still long enough to allow for a measureable amount of absorption. For example, a 6 mm diameter×10 mm long cylinder (having a volume about equal to 0.3 cc) in a standard plate is used for the near-IR, and a similar plate design with a cylinder having a 1 mm path length is used for the mid-IR. An example of one design is schematically illustrated in FIG. 3.

The sample chamber should be isolated from stray IR radiation. For example, a person walking into the area where the experiment is being performed provides a measurable amount of reflected heat radiation that may be picked up by the FPA. A closed sample chamber similar to those found in commercial FT-IRs is typically acceptable.

The FPA of the camera should have a high signal to noise ratio to measure the weak signal coming from each element (i.e., reactor) in the library. The exact limits are set by the amount of intensity provided by the source and by the amount lost in the system. Commercial IR cameras have FPAs made primarily of cooled InSb and HgCdTe detectors with fixed noise characterstics. Since the camera is typically purchased as a finished package, the sensitivity of the FPA is not the important factor rather, it is the sensitivity of the entire camera (FPA, electronics, filtering, etc.) that is the critical design factor.

In order to track chemical reactions with this device, the IR spectrum needs to be sampled at certain time intervals that may range from every 20 seconds to a single measurement depending on the desired information (i.e. in situ measurements vs. film characterization). Capturing the IR spectrum for every element in the library every 20 seconds requires a high speed IR camera; the data acquisition rate of the camera is determined by the strength of the signal, the desired spectral bandwidth, and the resolution. Although the true time required to obtain a spectrum relies on the data acquisition rate and on the computer processing, the ability of the IR camera to operate at faster than 120 frames/sec allows a sufficient number of interferograms to be sampled to reconstruct the spectrum rapidly.

The images captured by the IR camera should be collected and analyzed to create a series of interferograms (intensity versus time) for each element in the image corresponding to an element in the combinatorial library. The interferograms must be transformed back to a more useful intensity versus wavelength representation with the aide of a Fourier transform performed by the computer. In order to perform the Fourier transform, the computer must know precisely the time or mirror position corresponding to each image. It is therefore necessary to have an electronic trigger on the interferometer to trigger the camera shutter. In this way a series of plots of absorbance versus wavelength can be constructed for every element within the field of view of the infrared camera.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed:

1. A method of characterizing a relative thermal diffusivity for a plurality of materials, comprising the steps of:
   providing a thermally uniform substrate
   having a combinatorial array comprising a plurality of diverse materials at known locations on a first surface of said substrate;
   irradiating a second surface of said substrate with an infrared source;
   modulating said infrared source; and
   monitoring a temperature change associated with each of said plurality of materials as a function of time, said temperature change indicative of said relative thermal diffusivity of said plurality of materials.

2. The method of claim 1, wherein said plurality of diverse materials is deposited on said substrate.

3. The method of claim 1, wherein said irradiating step includes directing energy directly adjacent to a single element.

4. The method of claim 1, wherein said irradiating step includes directing energy to uniformly irradiate said plurality of diverse materials.

5. The method of claim 4, wherein said infrared source simultaneously and uniformly radiates entirety of said substrate.

6. The method of claim 1, wherein said temperature change is monitored with an infrared detector.

7. The method of claim 6, wherein said monitoring step includes repositioning said detector.

8. The method of claim 6, wherein said monitoring step includes repositioning said library relative to said detector.

9. The method of claim 6, wherein said detector includes a position sensitive detector array and said detector monitors the temperature change of said plurality of diverse materials.

10. The method of claim 1, wherein said thermal diffusivity is determined in the absence of data about the density and specific heat of said materials.

11. A system for characterizing a relative thermal diffusivity for a plurality of materials, comprising;
    a thermally uniform substrate adapted for containing an array of materials on a first surface of said substrate;
    a modulated IR radiation source for directing modulated IR radiation at a second surface of said substrate, wherein said IR radiation is substantially uniform across at least one material of said plurality of materials;
    an IR detector for monitoring a temperature change associated with said at least one material of said plurality of materials as a function of time, said IR detector adapted for outputting a signal corresponding to a monitored temperature;
    a translation stage system coupled to said substrate and said IR detector, said translation stage adapted for repositioning said substrate and said IR detector so that said IR detector sequentially monitors said temperature change as a function of time for each material of said plurality of materials, and wherein each material of said plurality of materials receives substantially equivalent IR radiation from said IR radiation source; and
    a processor coupled to said IR detector, wherein said processor records said output signals from said detector and determines said relative thermal diffusivity of said plurality of materials.

12. A system for characterizing a relative thermal diffusivity for a plurality of materials, comprising:
    a thermally uniform substrate adapted for containing a plurality of at least 9 different materials on a first surface of said substrate;
    a modulated IR radiation source for directing modulated IR radiation at a second surface of said substrate, wherein said IR radiation is substantially uniform across said plurality of materials;
    an IR detector array for monitoring a temperature change associated with each material of said plurality of materials as a function of time, said IR detector adapted for outputting a plurality of signals corresponding to said monitored temperature change for each material; and
    a processor coupled to said IR detector array, wherein said processor is adapted for recording said output signals from said detector array and determining said relative thermal diffusivity of said plurality of materials.

13. A method of characterizing a relative thermal diffusivity for a plurality of uncharacterized materials, comprising the steps of:
    providing a thermally uniform substrate;
    synthesizing a combinatorial array consisting essentially of a plurality of diverse uncharacterized materials at known locations on a first surface of said substrate, which differ in composition, stoichiometry or thickness;
    without removing said materials from said substrate, irradiating a second surface of said substrate with an infrared source;
    modulating said infrared source; and
    monitoring a temperature change associated with each of said plurality of materials as a function of time, said temperature change indicative of said relative thermal diffusivity of said plurality of materials.

14. The method of claim 13, wherein said plurality of diverse uncharacterized materials is deposited on said substrate.

15. The method of claim 13, wherein said irradiating step includes directing energy directly adjacent to a single element.

16. The method of claim 13, wherein said irradiating step includes directing energy to uniformly irradiate said plurality of diverse newly discovered materials.

17. The method of claim 13, wherein said infrared source simultaneously and uniformly radiates entirety of said substrate.

18. The method of claim 13, wherein said temperature change is monitored with an infrared detector.

19. The method of claim 18, wherein said monitoring step includes repositioning said detector.

20. The method of claim 19, wherein said monitoring step includes repositioning said library relative to said detector.

21. The method of claim 18, wherein said detector includes a position sensitive detector array and said detector monitors the temperature change of said plurality of diverse uncharacterized materials.

22. The method of claim 13, wherein the area upon which each material is synthesized is less than 1 $cm^2$.

23. The method of claim 13, wherein the area upon which each material is synthesized is less than 1 $mm^2$.

24. The method of claim 13, wherein the area upon which each material is synthesized is less than 0.5 $mm^2$.

25. The method of claim 13, further comprising preparing at least one of said materials on a bulk scale to exhibit substantially similar properties as exhibited in said array.

26. The method of claim 13, wherein said thermal diffusivity is determined in the absence of data about the density and specific heat of said materials.

27. The method of claim 13, further comprising preparing at least one of said materials in larger quantities to exhibit substantially similar properties as exhibited in said array.

28. The method of claim 13, wherein said substrate is thermally transparent.

29. A method of characterizing a relative thermal diffusivity for a plurality of uncharacterized materials, comprising the steps of:

provided a combinatorial array comprising materials located on a thermally uniform substrate at known locations within the array;

inducing a temperature change in said materials with a modulated infrared source;

scanning said array with an infrared detector for monitoring said temperature change associated with each of said plurality of uncharacterized materials as a function of time, thereby being capable of indicating relative thermal diffusivity of said plurality of materials in the absence of data about density and specific heat of said plurality of materials; and comparing materials within said array with respect to their relative thermal diffusivity performance.

30. The method of claim 29, further comprising synthesizing via vapor deposition said plurality of diverse materials at known locations on said array.

31. The method of claim 29, wherein the number of said materials on said array is at least about 9.

32. The method of claim 31, wherein said substrate is thermally transparent.

33. The method of claim 32, wherein said monitoring step includes repositioning said library and said detector relative to each other.

34. The method of claim 32, wherein the area upon which each material is provided on said substrate is less than about 1 cm$^2$.

35. The method of claim 34, wherein said comparing step includes ranking said materials within said array with respect to their thermal diffusivity performance.

36. The method of claim 34, further comprising preparing at least one of said materials on a bulk scale to exhibit substantially similar properties as exhibited in said array.

37. The method of claim 31, wherein said detector is an infrared focal plane array detector.

38. The method of claim 29, wherein the number of said materials on said array is at least about 50.

39. The method of claim 29, wherein the number of said materials on said array is at least about 100.

\* \* \* \* \*

UNITED STATES PATENT AND TRADEMARK OFFICE
CERTIFICATE OF CORRECTION

PATENT NO.     : 6,541,271 B1
DATED          : April 1, 2003
INVENTOR(S)    : McFarland et al.

It is certified that error appears in the above-identified patent and that said Letters Patent is hereby corrected as shown below:

Column 20,
Line 49, replace "13" after the word "claim" with -- 16 --

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,541,271 B1
DATED           : April 1, 2003
INVENTOR(S)     : McFarland et al.

It is certified that error appears in the above-identified patent and that said Letters Patent is hereby corrected as shown below:

Column 20,
Line 49, replace "13" after the word "claim" with -- 16 --

Signed and Sealed this

Thirtieth Day of September, 2003

JAMES E. ROGAN
*Director of the United States Patent and Trademark Office*